(12) United States Patent
Ye et al.

(10) Patent No.: US 12,228,478 B1
(45) Date of Patent: Feb. 18, 2025

(54) SYSTEM AND METHOD FOR SAMPLING METAL IONS IN CORROSIVE GAS

(71) Applicant: GUANGDONG HUATE GAS CO., LTD., Foshan (CN)

(72) Inventors: Xiangping Ye, Foshan (CN); Zhuhong Fu, Foshan (CN); Yanshan Chen, Foshan (CN); Yonghao Liang, Foshan (CN)

(73) Assignee: GUANGDONG HUATE GAS CO., LTD., Foshan (CN)

( * ) Notice: Subject to any disclaimer, the term of this patent is extended or adjusted under 35 U.S.C. 154(b) by 0 days.

(21) Appl. No.: 18/797,540

(22) Filed: Aug. 8, 2024

Related U.S. Application Data

(63) Continuation of application No. PCT/CN2024/085727, filed on Apr. 3, 2024.

(30) Foreign Application Priority Data

Aug. 10, 2023 (CN) .......................... 202311009968.6

(51) Int. Cl.
*G01N 1/22* (2006.01)
*G01N 1/38* (2006.01)

(52) U.S. Cl.
CPC ............. *G01N 1/2247* (2013.01); *G01N 1/38* (2013.01); *G01N 2001/385* (2013.01)

(58) Field of Classification Search
CPC ... G01N 1/2247; G01N 1/38; G01N 2001/385
See application file for complete search history.

(56) References Cited

FOREIGN PATENT DOCUMENTS

| | | |
|---|---|---|
| CN | 106226138 A | 12/2016 |
| CN | 112067375 A | 12/2020 |
| CN | 112629951 A | 4/2021 |
| CN | 216747605 U | 6/2022 |
| CN | 116087313 A | 5/2023 |
| CN | 116907925 A | 10/2023 |
| CN | 220794755 U | 4/2024 |
| KR | 20060073833 A | 6/2006 |
| KR | 102542740 B1 | 6/2023 |
| WO | 2005057177 A1 | 6/2005 |

*Primary Examiner* — Tarun Sinha
(74) *Attorney, Agent, or Firm* — Bayramoglu Law Offices LLC

(57) ABSTRACT

A system and method for sampling metal ions in a corrosive gas is provided. The system includes: a sampling bottle; a vacuuming pipeline provided with a vacuuming device, where the vacuuming device is configured to vacuum a sampling chamber; a replacement gas pipeline configured to blow a replacement gas into the sampling chamber; an injection pipeline configured to inject a sample gas into the sampling chamber; and a purge gas pipeline. With the sampling system, the sampling bottle can be first subjected to vacuuming and thorough replacement to reduce the interference of impurities, then the sampling bottle is introduced with a corrosive sample gas, and then a corrosive gas is vaporized and blown away through a purge gas to leave metal ions or metal ions are dissolved in an absorption solution.

8 Claims, 1 Drawing Sheet

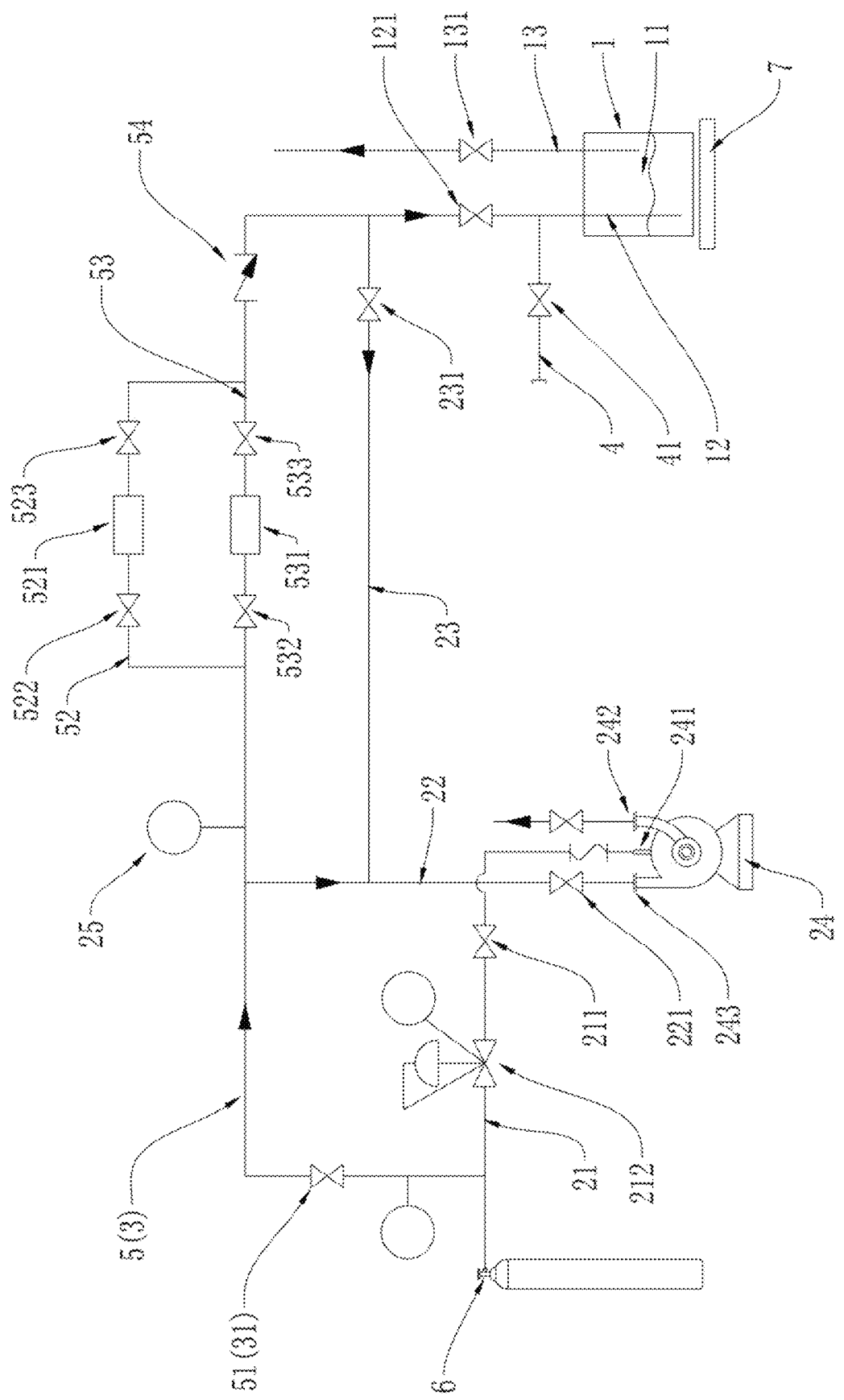

SYSTEM AND METHOD FOR SAMPLING METAL IONS IN CORROSIVE GAS

CROSS REFERENCE TO THE RELATED APPLICATIONS

This application is a continuation application of International Application No. PCT/CN2024/085727, filed on Apr. 3, 2024, which is based upon and claims priority to Chinese Patent Application No. 202311009968.6, filed on Aug. 10, 2023, the entire contents of which are incorporated herein by reference.

TECHNICAL FIELD

The present disclosure relates to the technical field of gas detection, and in particular to a system and method for sampling metal ions in a corrosive gas.

BACKGROUND

In recent years, with the rapid upgrading in the technical field of integrated circuits, the wafer size has developed from 6 inches and 8 inches to 12 inches, and the process technology has developed from 28 nm, 14 nm, and 7 nm to 5 nm, and even to 3 nm and 1 nm in the future. As a result, advanced requirements are put forward for the purity of the gas, and the gas needs to be ultra-pure and ultra-clean. The ultra-pure requirement means that the purity of the gas needs to reach 4.5 N, 5 N, 6 N, 7 N, or even higher. The ultra-clean requirement means that the content of particles and metal impurities needs to be strictly controlled. The increase in purity by every N and the decrease in concentrations of particles and metal impurities by every order of magnitude will result in a significant increase in process complexity and difficulty. During the analysis of trace metal ions in the gas, the sampling system, the solvent, the container, or the like all have an impact on the analysis result, such that the analysis result is prone to an accidental error or even a mistake. As a result, especially for corrosive gases, strict requirements need to be met for the sampling of metal ions and the analysis system and method.

However, the existing sampling system and method cannot allow the accurate sampling of metal ions in a corrosive gas, such that the analysis is prone to errors or even mistakes, resulting in high requirements for the corrosion resistance of the analysis system.

SUMMARY

A major objective of the present disclosure is to provide a system and method for sampling metal ions in a corrosive gas. The present disclosure is intended to solve the technical problem that the existing technology cannot allow the enough accurate sampling of metal ions in a corrosive gas and has high requirements for corrosion resistance of a system, resulting in an error or even a mistake of analysis.

In order to allow the above objective, the present disclosure provides a system for sampling metal ions in a corrosive gas, including:
  a sampling bottle internally provided with a sampling chamber, where the sampling bottle is provided with a first sampling pipeline and a second sampling pipeline that communicate with the sampling chamber, and the second sampling pipeline is provided with a discharge valve;
  a vacuuming pipeline connected with the first sampling pipeline, where the vacuuming pipeline is provided with a first vacuuming valve, the vacuuming pipeline is provided with a vacuuming device, and the vacuuming device is configured to vacuum the sampling chamber;
  a replacement gas pipeline connected with the first sampling pipeline, where the replacement gas pipeline is provided with a replacement valve, and the replacement gas pipeline is configured to blow a replacement gas into the sampling chamber;
  an injection pipeline connected with the first sampling pipeline, where the injection pipeline is provided with an injection valve, and the injection pipeline is configured to inject a sample gas into the sampling chamber; and
  a purge gas pipeline connected with the first sampling pipeline, where the purge gas pipeline is provided with a purge valve, and the purge gas pipeline is configured to slowly blow a purge gas into the sampling chamber and blow away a corrosive gas in the sample gas.

After the vacuuming pipeline vacuums the sampling bottle and the replacement gas pipeline blows a replacement gas into the sampling bottle alternately, water, air, and other impurities in the sampling chamber can be replaced completely. Then the vacuuming pipeline and the replacement gas pipeline are closed and the injection pipeline is opened, such that a sample gas to be detected enters the sampling bottle through the injection pipeline. Different sampling modes are adopted for a low-pressure liquefied gas and a high-pressure liquefied gas: For the low-pressure liquefied gas, the discharge valve is closed, and the sample gas is sampled by the sampling bottle. When an enough amount of the sample gas is sampled, the injection pipeline is closed, and the purge gas pipeline and the discharge valve are opened, such that a purge gas is slowly introduced into the sampling bottle, a liquefied corrosive gas is vaporized and blown away by the purge gas to flow out through the second sampling pipeline, and metal ions do not flow away with the purge gas and remain in the sampling bottle for subsequent detection and analysis. For the high-pressure liquefied gas, the sampling bottle is provided with an absorption solution capable of dissolving metal ions. When the sample gas enters the sampling bottle, the discharge valve is opened, such that the sample gas slowly enters the absorption solution, metal ions in the sample gas are dissolved in the absorption solution, and a corrosive gas flows out through the second sampling pipeline. After the sampling, the metal ions in the absorption solution can be analyzed.

With the sampling system, the sampling bottle can be first subjected to vacuuming and thorough replacement to reduce the interference of impurities, then the sampling bottle is introduced with a corrosive sample gas, and then a corrosive gas is blown away through the purge gas, or metal ions are dissolved in an absorption solution such that the metal ions are left in the sampling bottle for subsequent detection and analysis, which can not only accurately sample the metal ions in the corrosive gas, but also reduce the requirements for corrosion resistance of a sampling system and a detection and analysis system.

Preferably, the purge gas pipeline includes the replacement gas pipeline and the purge valve is the replacement valve. When the purge gas pipeline and the replacement gas pipeline are the same pipeline, it can reduce the number of pipelines and simplify the sampling system.

Preferably, the vacuuming device is a vacuum generator, and the vacuum generator includes a gas inlet port, a gas outlet port, and a negative pressure port; the vacuuming pipeline includes a vacuum power pipeline, a second vacuum pipeline, and a third vacuum pipeline; one end of the vacuum power pipeline is connected with the gas inlet port; one end of the second vacuum pipeline is connected with the negative pressure port; and one end of the third vacuum pipeline is connected with the second vacuum pipeline, and the other end of the third vacuum pipeline is connected with the first sampling pipeline.

One end of the purge gas pipeline is connected with the first sampling pipeline, and the other end of the purge gas pipeline is connected with the other end of the vacuum power pipeline and is provided with a gas source inlet; the other end of the second vacuum pipeline is connected with the purge gas pipeline; the first vacuuming valve is arranged on the third vacuum pipeline; the vacuum power pipeline is provided with a vacuum power valve and the second vacuum pipeline is provided with a second vacuuming valve; a location of the second vacuuming valve is closer to the negative pressure port than a junction of the second vacuum pipeline and the third vacuum pipeline; and a location of the purge valve is closer to the gas source inlet than a junction of the purge gas pipeline and the second vacuum pipeline.

The first sampling pipeline is provided with a first valve; a junction of the injection pipeline and the first sampling pipeline is closer to a location of the sampling bottle than the first valve; and a location of the first valve is closer to the sampling bottle than a junction of the third vacuum pipeline and the first sampling pipeline and a junction of the purge gas pipeline and the first sampling pipeline.

The gas source inlet is connected with a gas source, such that a same gas source can be used to replace a gas, purge a gas, and generate a power for vacuuming, which can reduce the number of gas sources.

Preferably, the purge gas pipeline is provided with a mass flow rate control device, and the mass flow rate control device is configured to regulate a flow rate of the purge gas blown into the sampling chamber. The mass flow rate control device can regulate the flow rate of the purge gas to make the purge gas introduced into the sampling chamber at an appropriate speed, such that the purge gas will not take away metal ions or will take away merely a small number of metal ions.

Preferably, the mass flow rate control device includes a first mass flow rate controller and a second mass flow rate controller; the purge gas pipeline is provided with a first shunt and a second shunt that are arranged in parallel; the first shunt is provided with a third valve and a fourth valve, and the first mass flow rate controller is arranged between the third valve and the fourth valve; and the second shunt is provided with a fifth valve and a sixth valve, and the second mass flow rate controller is arranged between the fifth valve and the sixth valve. Since the first shunt, the second shunt, the first mass flow rate controller, and the second mass flow rate controller are provided, the first mass flow rate controller and the second mass flow rate controller can be used alternately to control the flow rate of the purge gas, which can avoid a failure and ensure a continuous operation.

Preferably, the system for sampling metal ions in a corrosive gas further includes a weight detection device, where the weight detection device is configured to support the sampling bottle, and the weight detection device is capable of detecting a weight change value of the sampling bottle.

When the sample gas enters the sampling chamber and is sampled, a weight gain of the sample gas can be detected by the weight detection device, so as to quantitatively control a sampled amount of the sample gas.

Preferably, materials for the sampling bottle and the injection pipeline both are perfluoroalkoxy. The perfluoroalkoxy has strong corrosion resistance and can adapt to the use of various corrosive gases.

In another aspect, the present disclosure also provides a sampling method using the system for sampling metal ions in a corrosive gas described above, including the following steps:

A1: closing the discharge valve, the injection valve, and the purge valve and opening the vacuum power valve, the first vacuuming valve, the second vacuuming valve, and the first valve to make a gas source enter the vacuum power pipeline and the gas inlet port of the vacuum generator through the gas source inlet and then flow out through the gas outlet port of the vacuum generator, such that the negative pressure port of the vacuum generator generates a negative pressure to vacuum the second vacuum pipeline, the third vacuum pipeline, the first sampling pipeline, the purge gas pipeline, and the sampling bottle;

A2: closing the vacuum power valve, the first vacuuming valve, and the second vacuuming valve and opening the discharge valve and the purge valve, such that a replacement gas source enters the purge gas pipeline through the gas source inlet, flows into the first sampling pipeline and the sampling bottle, and then flows out through the second sampling pipeline;

A3: alternately conducting the step A1 and the step A2 multiple times with the step A1 as the last step, and closing the vacuum power valve, the first vacuuming valve, and the second vacuuming valve;

A4: closing the discharge valve and the first valve and opening the injection valve to make a low-pressure liquefied gas to be sampled introduced into the sampling bottle, collecting the sample gas by the sampling bottle quantitatively, where a lower end of the first sampling pipeline is located under a liquid level of a sampled low-pressure liquefied gas, and a lower end of the second sampling pipeline is located above the liquid level of the sampled low-pressure liquefied gas; and A5: closing the injection valve and opening the purge valve, the first valve, and the discharge valve to make a purge gas source enter the purge gas pipeline through the gas source inlet and then flow into the first sampling pipeline and the sampling bottle, where the purge gas is introduced at a flow rate of 100 mL/min to 200 mL/min to slowly vaporize a liquefied corrosive gas in the sample gas and purge a vaporized corrosive gas out of the sampling bottle through the second sampling pipeline, such that the metal ions remain in the sampling bottle. At this flow rate, the purge gas can vaporize and take away the liquefied corrosive gas without taking away metal ions or only taking away a very small number of metal ions, and this flow rate is not too low and can avoid a too-long purge time.

In the sampling method, the sampling bottle is first subjected to vacuuming and replacement such that the sampling bottle and other pipelines of the entire sampling system undergo thorough replacement to reduce the interference of impurities, then the sampling bottle is introduced with a low-pressure liquefied gas as a corrosive sample, and then the liquefied corrosive gas is vaporized and blown away through the purge gas to leave metal ions in the sampling bottle for subsequent detection and analysis, which can not only accurately sample the metal ions in the corrosive gas, but also reduce the requirements for corrosion resistance of a sampling system and a detection and analysis system.

Preferably, the purge gas pipeline is provided with a first shunt and a second shunt that are arranged in parallel; the first shunt is provided with a third valve and a fourth valve, and the first shunt is provided with a first mass flow rate controller; the first mass flow rate controller is arranged between the third valve and the fourth valve; the second shunt is provided with a second mass flow rate controller, and the second shunt is provided with a fifth valve and a sixth valve; the second mass flow rate controller is arranged between the fifth valve and the sixth valve; and a junction of the second vacuum pipeline and the purge gas pipeline is located between the purge valve and the first shunt as well as the second shunt;

in the step A1, while the vacuum power valve, the first vacuuming valve, the second vacuuming valve, and the first valve are opened, the third valve and the fourth valve are opened and/or the fifth valve and the sixth valve are opened to vacuum the first shunt and/or the second shunt; and in the step A5, while the purge valve, the first valve, and the discharge valve are opened, the third valve and the fourth valve are opened and/or the fifth valve and the sixth valve are opened, and the first mass flow rate controller and/or the second mass flow rate controller control(s) the flow rate of the purge gas.

The first mass flow rate controller and the second mass flow rate controller can be used alternately to control the flow rate of the purge gas, which can avoid a failure and ensure a continuous operation. During the vacuuming and replacement, the first shunt and/or the second shunt and the first mass flow rate controller and/or the second mass flow rate controller can undergo vacuuming and replacement, such that impurities can be reduced before the sampling and purging steps of the sampling system to improve the accuracy of sampling.

In another aspect, the present disclosure also provides a sampling method using the system for sampling metal ions in a corrosive gas described above, including the following steps:

B1: adding an absorption solution capable of dissolving the metal ions to the sampling bottle, where a lower end of the first sampling pipeline is located under a liquid level of the absorption solution, and a lower end of the second sampling pipeline is located above the liquid level of the absorption solution; and B2: closing the first valve and opening the discharge valve and the injection valve, such that a high-pressure liquefied gas to be sampled is introduced into the sampling bottle to enter the absorption solution, the metal ions in the gas are dissolved in the absorption solution, and a corrosive gas is discharged through the discharge valve.

For the high-pressure liquefied gas, the sampling bottle is provided with an absorption solution capable of dissolving the metal ions. When the sample gas enters the sampling bottle, the discharge valve is opened, such that the sample gas slowly enters the absorption solution, the metal ions in the sample gas are dissolved in the absorption solution, and a corrosive gas flows out through the second sampling pipeline. After the sampling, the metal ions in the absorption solution can be analyzed.

BRIEF DESCRIPTION OF THE DRAWINGS

To describe the technical solutions in the embodiments of the present disclosure or in the prior art clearly, the accompanying drawing required for describing the embodiments or the prior art will be briefly described below. Apparently, the accompanying drawing in the following description only shows some embodiments of the present disclosure, and those skilled in the art may still derive other accompanying drawings according to the structure shown in the accompanying drawing without creative efforts.

FIGURE is a schematic structural diagram of the system for sampling metal ions in a corrosive gas provided by the present disclosure.

In this FIGURE: 1—sampling bottle, 11—sampling chamber, 12—first sampling pipeline, 121—first valve, 13—second sampling pipeline, 131—discharge valve, 21—vacuum power pipeline, 211—vacuum power valve, 212—pressure regulating valve, 22—second vacuum pipeline, 221—second vacuuming valve, 23—third vacuum pipeline, 231—first vacuuming valve, 24—vacuuming device, 241—gas inlet port, 242—gas outlet port, 243—negative pressure port, 25—vacuum gauge, 3—replacement gas pipeline, 31—replacement valve, 4—injection pipeline, 41—injection valve, 5—purge gas pipeline, 51—purge valve, 52—first shunt, 521—first mass flow rate controller, 522—third valve, 523—fourth valve, 53—second shunt, 531—second mass flow rate controller, 532—fifth valve, 533—sixth valve, 54—one-way valve, 6—gas source inlet, and 7—weight detection device.

The implementation of the objective, the functional characteristics, and the advantages of the present disclosure will be further described below with reference to the embodiments and accompanying drawing.

DETAILED DESCRIPTION OF THE EMBODIMENTS

The technical solutions of the embodiments of the present disclosure are clearly and completely described below with reference to the accompanying drawings in the embodiments of the present disclosure. Apparently, the described embodiments are merely some rather than all of the embodiments of the present disclosure. All other embodiments obtained by those skilled in the art based on the embodiments of the present disclosure without creative efforts should fall within the protection scope of the present disclosure.

It should be noted that all the directional indications (such as upper, lower, left, right, front, and rear) in the embodiments of the present disclosure are used merely to explain relative position relationships, motion situations, or the like of components in specific gestures. If the specific gestures change, the directional indications also change accordingly.

Moreover, the terms such as "first", "second", or the like described in the embodiments of the present disclosure are used herein only for the purpose of description and are not intended to indicate or imply relative importance, or implicitly indicate the number of indicated technical features. Therefore, features defined by "first" and "second" may explicitly or implicitly include at least one of the features. Further, the technical solutions of various embodiments may be combined with each other, but it must be on the basis that a combination thereof can be implemented by those skilled in the art. In case of a contradiction with the combination of the technical solutions or a failure to implement the combination, it should be considered that the combination of the technical solutions does not exist, and is not within the protection scope of the present disclosure.

As shown in the FIGURE, a system for sampling metal ions in a corrosive gas is provided, including sampling bottle 1, a vacuuming pipeline, replacement gas pipeline 3, injection pipeline 4, and purge gas pipeline 5.

Sampling chamber 11 is provided inside the sampling bottle 1, the sampling bottle 1 is provided with first sampling pipeline 12 and second sampling pipeline 13 that communicate with the sampling chamber 11, and the second sampling pipeline 13 is provided with discharge valve 131.

The vacuuming pipeline is connected with the first sampling pipeline 12, the vacuuming pipeline is provided with first vacuuming valve 231, the vacuuming pipeline is provided with vacuuming device 24, and the vacuuming device 24 is configured to vacuum the sampling chamber 11. During vacuuming, the first vacuuming valve 231 is opened, the discharge valve 131 is closed, and the vacuuming device 24 operates to generate a negative pressure. The vacuuming device 24 can be a vacuum pump or the like.

The replacement gas pipeline 3 is connected with the first sampling pipeline 12, the replacement gas pipeline 3 is provided with replacement valve 31, and the replacement gas pipeline 3 is configured to blow a replacement gas into the sampling chamber 11. During replacement, the replacement valve 31 and the discharge valve 131 are opened to make a replacement gas enter the sampling chamber 11 through the replacement gas pipeline 3 and the first sampling pipeline 12 and blow water, air, and other impurities in the sampling chamber 11 out, such that the sampling chamber 11 is full of the replacement gas. The replacement gas can be nitrogen.

The injection pipeline 4 is connected with the first sampling pipeline 12, the injection pipeline 4 is provided with injection valve 41, and the injection pipeline 4 is configured to inject a sample gas into the sampling chamber 11. When a corrosive gas is injected, the injection valve 41 is opened and the discharge valve 131 is closed, such that the sampling chamber 11 is full of the corrosive gas.

The purge gas pipeline 5 is connected with the first sampling pipeline 12, the purge gas pipeline 5 is provided with purge valve 51, and the purge gas pipeline 5 is configured to slowly blow a purge gas into the sampling chamber 11 and blow away a corrosive gas in the sample gas. During purging, the purge valve 51 and the discharge valve 131 are opened, such that the purge gas slowly enters the sampling chamber 11 and the corrosive gas is taken away and discharged through the second sampling pipeline 13. The purge gas can be nitrogen.

After the vacuuming pipeline vacuums the sampling bottle 1 and the replacement gas pipeline 3 blows a replacement gas into the sampling bottle 1 alternately, water, air, and other impurities in the sampling chamber 11 can be replaced completely. Then the vacuuming pipeline and the replacement gas pipeline 3 are closed and the injection pipeline 4 is opened, such that a sample gas to be detected enters the sampling bottle 1 through the injection pipeline 4. Different sampling modes are adopted for a low-pressure liquefied gas and a high-pressure liquefied gas: For the low-pressure liquefied gas, the discharge valve 131 is closed, and the sample gas is sampled by the sampling bottle 1. When an enough amount of the sample gas is sampled, the injection pipeline 4 is closed, and the purge gas pipeline and the discharge valve 131 are opened, such that a purge gas is slowly introduced into the sampling bottle 1, a liquefied corrosive gas is vaporized and blown away by the purge gas to flow out through the second sampling pipeline 13, and metal ions are heavy, do not flow away with the purge gas, and remain in the sampling bottle 1 for subsequent detection and analysis. For the high-pressure liquefied gas, the sampling bottle 1 is provided with an absorption solution capable of dissolving metal ions. When the sample gas enters the sampling bottle 1, the discharge valve 131 is opened, such that the sample gas slowly enters the absorption solution, metal ions in the sample gas are dissolved in the absorption solution, and a corrosive gas flows out through the second sampling pipeline 13. After the sampling, the metal ions in the absorption solution can be analyzed.

With the sampling system, the sampling bottle 1 can be first subjected to vacuuming and thorough replacement to reduce the interference of impurities, then the sampling bottle 1 is introduced with a corrosive sample gas, and then a corrosive gas is blown away through the purge gas, or metal ions are dissolved in the absorption solution such that metal ions are left in the sampling bottle 1 for subsequent detection and analysis, which can not only accurately sample the metal ions in the corrosive gas, but also reduce the requirements for corrosion resistance of a sampling system and a detection and analysis system.

In some specific embodiments, the purge gas pipeline 5 includes the replacement gas pipeline 3 and the purge valve 51 is the replacement valve 31. When the purge gas pipeline 5 and the replacement gas pipeline 3 are the same pipeline, it can reduce the number of pipelines and simplify the sampling system. In some other embodiments, the purge gas pipeline 5 and the replacement gas pipeline 3 can be different pipelines, which can also allow the replacement and purging effects.

Further, the vacuuming device 24 is a vacuum generator, and the vacuum generator includes gas inlet port 241, gas outlet port 242, and negative pressure port 243. The vacuuming pipeline includes vacuum power pipeline 21, second vacuum pipeline 22, and third vacuum pipeline 23. One end of the vacuum power pipeline 21 is connected with the gas inlet port 241. One end of the second vacuum pipeline 22 is connected with the negative pressure port 243. One end of the third vacuum pipeline 23 is connected with the second vacuum pipeline 22, and the other end of the third vacuum pipeline 23 is connected with the first sampling pipeline 12.

One end of the purge gas pipeline 5 is connected with the first sampling pipeline 12, and the other end of the purge gas pipeline 5 is connected with the other end of the vacuum power pipeline 21 and is provided with gas source inlet 6. The other end of the second vacuum pipeline 22 is connected with the purge gas pipeline 5. The first vacuuming valve 231 is arranged on the third vacuum pipeline 23. The vacuum power pipeline 21 is provided with vacuum power valve 211 and the second vacuum pipeline 22 is provided with second vacuuming valve 221. A location of the second vacuuming valve 221 is closer to the negative pressure port 243 than a junction of the second vacuum pipeline 22 and the third vacuum pipeline 23. A location of the purge valve 51 is closer to the gas source inlet 6 than a junction of the purge gas pipeline 5 and the second vacuum pipeline 22.

The first sampling pipeline 12 is provided with first valve 121. A junction of the injection pipeline 4 and the first sampling pipeline 12 is closer to the sampling bottle 1 than a location of the first valve 121. A location of the first valve 121 is closer to the sampling bottle 1 than a junction of the third vacuum pipeline 23 and the first sampling pipeline 12 and a junction of the purge gas pipeline 5 and the first sampling pipeline 12.

The gas source inlet 6 is connected with a gas source, such that a same gas source can be used to replace a gas, purge a gas, and generate a power for vacuuming, which can reduce the number of gas sources. The gas source can be nitrogen.

A sampling method using the system for sampling metal ions in a corrosive gas described above is also provided, including the following steps:

Step A1: The discharge valve 131, the injection valve 41, and the purge valve 51 are closed and the vacuum power valve 211, the first vacuuming valve 231, the second vacuuming valve 221, and the first valve 121 are opened to make a gas source enter the vacuum power pipeline 21 and the gas inlet port 241 of the vacuum generator through the gas source inlet 6 and then flow out through the gas outlet port 242 of the vacuum generator, such that the negative pressure port 243 of the vacuum generator generates a negative pressure to vacuum the second vacuum pipeline 22, the third vacuum pipeline 23, the first sampling pipeline 12, the purge gas pipeline 5, and the sampling bottle 1.

The negative pressure port 243 of the vacuum generator generates a negative pressure such that a negative pressure is generated in the second vacuum pipeline 22, the third vacuum pipeline 23, and the sampling bottle 1 successively, and the second vacuum pipeline 22 is also connected to the purge gas pipeline 5 such that air in the purge gas pipeline 5 is also pumped out, which can further reduce impurities in the sampling system. The vacuum power pipeline 21 is provided with pressure regulating valve 212. The pressure regulating valve 212 can control a gas pressure of the gas source entering the vacuum generator to adjust a size of a negative pressure generated. The second vacuum pipeline 22, the third vacuum pipeline 23, or a purge pipeline can be provided with vacuum gauge 25 configured to detect a vacuum degree value during vacuuming. The vacuuming is stopped when a required vacuum degree value is reached.

Step A2: The vacuum power valve 211, the first vacuuming valve 231, and the second vacuuming valve 221 are closed and the discharge valve 131 and the purge valve 51 are opened to make a replacement gas source enter the purge gas pipeline 5 through the gas source inlet 6, flow into the first sampling pipeline 12 and the sampling bottle 1, and then flow out through the second sampling pipeline 13, such that the replacement gas blows air and impurities in the sampling system out.

Step A3: The step A1 and the step A2 are alternately conducted multiple times with the step A1 as the last step, and the vacuum power valve 211, the first vacuuming valve 231, and the second vacuuming valve 221 are closed. After the multiple times of vacuuming and replacement, there are few impurities in the sampling system, which can improve the sampling and detection accuracy. Since the last step is vacuuming, a negative pressure can be generated in the sampling bottle 1, which facilitates a low-pressure liquefied gas to enter the sampling bottle 1.

Step A4: The discharge valve 131 and the first valve 121 are closed and the injection valve 41 is opened to make a low-pressure liquefied gas to be sampled introduced into the sampling bottle 1, and the sample gas is collected by the sampling bottle 1 quantitatively, where a lower end of the first sampling pipeline 12 is located under a liquid level of a sampled low-pressure liquefied gas, and a lower end of the second sampling pipeline 13 is located above the liquid level of the sampled low-pressure liquefied gas.

Step A5: The injection valve 41 is closed and the purge valve 51, the first valve 121, and the discharge valve 131 are opened to make a purge gas source enter the purge gas pipeline 5 through the gas source inlet 6 and then flow into the first sampling pipeline 12 and the sampling bottle 1, the purge gas is introduced at a flow rate of 100 mL/min to 200 mL/min to slowly vaporize a liquefied corrosive gas in the sample gas and purge a vaporized corrosive gas out of the sampling bottle 1 through the second sampling pipeline 13, such that the metal ions remain in the sampling bottle 1.

In the sampling method, the sampling bottle 1 is first subjected to vacuuming and replacement such that the sampling bottle 1 and other pipelines of the entire sampling system undergo thorough replacement to reduce the interference of impurities, then the sampling bottle 1 is introduced with a corrosive sample gas, and then the liquefied corrosive gas is vaporized and blown away through the purge gas to leave metal ions in the sampling bottle 1 for subsequent detection and analysis, which can not only accurately sample the metal ions in the corrosive gas, but also reduce the requirements for corrosion resistance of a sampling system and a detection and analysis system. When the sampling is completed, the sampling bottle 1 is taken out from the sampling system, the metal ions are dissolved with a 5% G6-grade $HNO_3$ solution, and a content of the metal ions is analyzed by ICP-MS In the step A5 of the sampling method, the purge gas is introduced at a flow rate of 100 mL/min to 200 mL/min. At this flow rate, the purge gas can vaporize and take away the liquefied corrosive gas without taking away metal ions or only taking away a very small number of metal ions, and this flow rate is not too low and can avoid a too-long purge time.

In some specific embodiments, in the step A3, a volume of the sampling bottle 1 is 500 mL, and a purging time is 11 h to 13 h, which can completely vaporize and blow away a corrosive liquid and make only metal ions left in the sampling bottle 1.

In some specific embodiments, the purge gas pipeline 5 is provided with a mass flow rate control device, and the mass flow rate control device is configured to regulate a flow rate of the purge gas blown into the sampling chamber 11. The mass flow rate control device can regulate the flow rate of the purge gas to make the purge gas introduced into the sampling chamber 11 at an appropriate speed, such that the purge gas will not take away metal ions or will take away merely a small number of metal ions.

Further, the mass flow rate control device includes first mass flow rate controller 521 and second mass flow rate controller 531. The purge gas pipeline 5 is provided with first shunt 52 and second shunt 53 that are arranged in parallel. The first shunt 52 is provided with third valve 522 and fourth valve 523, and the first mass flow rate controller 521 is arranged between the third valve 522 and the fourth valve 523. The second shunt 53 is provided with fifth valve 532 and sixth valve 533, and the second mass flow rate controller 531 is arranged between the fifth valve 532 and the sixth valve 533.

Since the first shunt 52, the second shunt 53, the first mass flow rate controller 521, and the second mass flow rate controller 531 are provided, the first mass flow rate controller 521 and the second mass flow rate controller 531 can be used alternately to avoid a failure and ensure a continuous operation. In some embodiments, the purge gas pipeline 5 is provided with one-way valve 54. The one-way valve 54 is closer to the first sampling pipeline 12 than the first shunt 52 and the second shunt 53, which can prevent a corrosive gas from flowing into the purge gas pipeline 5.

Further, the purge gas pipeline 5 is provided with first shunt 52 and second shunt 53 that are arranged in parallel. The first shunt 52 is provided with third valve 522 and fourth valve 523, and the first shunt 52 is provided with first mass flow rate controller 521. The first mass flow rate controller 521 is arranged between the third valve 522 and the fourth valve 523. The second shunt 53 is provided with second mass flow rate controller 531, and the second shunt 53 is provided with fifth valve 532 and sixth valve 533. The second mass flow rate controller 531 is arranged between the fifth valve 532 and the sixth valve 533. A junction of the second vacuum pipeline 22 and the purge gas pipeline 5 is located between the purge valve 51 and the first shunt 52 as well as the second shunt 53.

In the step A1 of the sampling method, while the vacuum power valve 211, the first vacuuming valve 231, the second vacuuming valve 221, and the first valve 121 are opened, the third valve 522 and the fourth valve 523 are opened and/or the fifth valve 532 and the sixth valve 533 are opened to vacuum the first shunt 52 and/or the second shunt 53.

In the step A5, while the purge valve 51, the first valve 121, and the discharge valve 131 are opened, the third valve 522 and the fourth valve 523 are opened and/or the fifth valve 532 and the sixth valve 533 are opened, and the first mass flow rate controller 521 and/or the second mass flow rate controller 531 control(s) the flow rate of the purge gas.

The first mass flow rate controller 521 and the second mass flow rate controller 531 can be used alternately to control the flow rate of the purge gas, which can avoid a failure and ensure a continuous operation. During the vacuuming and replacement, the first shunt 52 and/or the second shunt 53 and the first mass flow rate controller 521 and/or the second mass flow rate controller 531 can undergo vacuuming and replacement, such that impurities can be reduced before the sampling and purging steps of the sampling system to improve the accuracy of sampling.

In some specific embodiments, the system for sampling metal ions in a corrosive gas further includes weight detection device 7. The weight detection device 7 is configured to support the sampling bottle 1, and the weight detection device 7 is capable of detecting a weight change value of the sampling bottle 1.

When the sample gas enters the sampling chamber 11 and is collected, a weight gain of the sample gas can be detected by the weight detection device 7, so as to quantitatively control a collected amount of the sample gas.

Another sampling method using the system for sampling metal ions in a corrosive gas described above is also provided, including the following steps:

Step B1: An absorption solution capable of dissolving the metal ions is added to the sampling bottle 1, where a lower end of the first sampling pipeline 12 is located under a liquid level of the absorption solution, and a lower end of the second sampling pipeline 13 is located above the liquid level of the absorbing solution.

Step B2: The first valve 121 is closed and the discharge valve 131 and the injection valve 41 are opened, such that a high-pressure liquefied gas to be sampled is introduced into the sampling bottle 1 at a flow rate of 20 mL/min to 100 mL/min to enter the absorption solution, the metal ions in the gas are dissolved in the absorption solution, and a corrosive gas is discharged through the discharge valve 131.

For the high-pressure liquefied gas, the sampling bottle 1 is provided with an absorption solution capable of dissolving the metal ions. The absorption solution can be a nitric acid solution, a hydrofluoric acid solution, or the like. When the sample gas enters the sampling bottle 1, the discharge valve 131 is opened, such that the high-pressure liquefied gas slowly enters the absorption solution with the help of its own high pressure, the metal ions in the sample gas are dissolved in the absorption solution, and a corrosive gas flows out through the second sampling pipeline. After the sampling, the metal ions in the absorption solution can be analyzed.

In some other embodiments, before the step B1, the replacement valve 31, the first valve 121, and the discharge valve 131 can be opened, such that the sampling bottle 1 is first purged with the replacement gas and impurities in the sampling bottle 1 are blown out, which can improve the accuracy of sampling.

In some specific embodiments, materials for the sampling bottle 1 and the injection pipeline 4 both are perfluoroalkoxy. The perfluoroalkoxy has strong corrosion resistance and can adapt to the use of various corrosive gases. The materials for the sampling bottle 1 and the injection pipeline 4 can also be a corrosion-resistant material such as polytetrafluoroethylene.

The above are merely preferred embodiments of the present disclosure, and the scope of the present disclosure is not limited thereto. Any equivalent structural change made using the content of the specification and the accompanying drawing of the present disclosure under the inventive concept of the present disclosure, or direct/indirect application thereof in other related technical fields, shall fall within the protection scope of the present disclosure.

What is claimed is:

1. A system for sampling metal ions in a corrosive gas, comprising:
    a sampling bottle internally provided with a sampling chamber, wherein the sampling bottle is provided with a first sampling pipeline and a second sampling pipeline, the first sampling pipeline and the second sampling pipeline are communicated with the sampling chamber, and the second sampling pipeline is provided with a discharge valve;
    a vacuuming pipeline connected with the first sampling pipeline, wherein the vacuuming pipeline is provided with a first vacuuming valve, the vacuuming pipeline is provided with a vacuuming device, and the vacuuming device is configured to vacuum the sampling chamber;
    a replacement gas pipeline connected with the first sampling pipeline, wherein the replacement gas pipeline is provided with a replacement valve, and the replacement gas pipeline is configured to blow a replacement gas into the sampling chamber;
    an injection pipeline connected with the first sampling pipeline, wherein the injection pipeline is provided with an injection valve, and the injection pipeline is configured to inject a sample gas into the sampling chamber; and
    a purge gas pipeline connected with the first sampling pipeline, wherein the purge gas pipeline is provided with a purge valve, and the purge gas pipeline is configured to slowly blow a purge gas into the sampling chamber and blow away a corrosive gas in the sample gas,
    wherein the purge gas pipeline comprises the replacement gas pipeline and the purge valve is the replacement valve;
    the vacuuming device is a vacuum generator, and the vacuum generator comprises a gas inlet port, a gas outlet port, and a negative pressure port; the vacuuming pipeline comprises a vacuum power pipeline, a second vacuum pipeline, and a third vacuum pipeline; a first end of the vacuum power pipeline is connected with the gas inlet port; a first end of the second vacuum pipeline is connected with the negative pressure port; and a first end of the third vacuum pipeline is connected with the second vacuum pipeline, and a second end of the third vacuum pipeline is connected with the first sampling pipeline;
    a first end of the purge gas pipeline is connected with the first sampling pipeline, and a second end of the purge gas pipeline is connected with a second end of the vacuum power pipeline and is provided with a gas source inlet; a second end of the second vacuum pipeline is connected with the purge gas pipeline; the first vacuuming valve is arranged on the third vacuum pipeline; the vacuum power pipeline is provided with a vacuum power valve, and the second vacuum pipeline is provided with a second vacuuming valve; a location of the second vacuuming valve is closer to the negative pressure port than a junction of the second vacuum pipeline and the third vacuum pipeline; and a location of the purge valve is closer to the gas source inlet than a junction of the purge gas pipeline and the second vacuum pipeline;

the first sampling pipeline is provided with a first valve; a junction of the injection pipeline and the first sampling pipeline is closer to the sampling bottle than a location of the first valve; and the location of the first valve is closer to the sampling bottle than a junction of the third vacuum pipeline and the first sampling pipeline and a junction of the purge gas pipeline and the first sampling pipeline.

2. The system for sampling the metal ions in the corrosive gas according to claim 1, wherein the purge gas pipeline is provided with a mass flow rate control device, and the mass flow rate control device is configured to regulate a flow rate of the purge gas blown into the sampling chamber.

3. The system for sampling the metal ions in the corrosive gas according to claim 2, wherein the mass flow rate control device comprises a first mass flow rate controller and a second mass flow rate controller; the purge gas pipeline is provided with a first shunt and a second shunt, and the first shunt and the second shunt are arranged in parallel; the first shunt is provided with a third valve and a fourth valve, and the first mass flow rate controller is arranged between the third valve and the fourth valve; and the second shunt is provided with a fifth valve and a sixth valve, and the second mass flow rate controller is arranged between the fifth valve and the sixth valve.

4. The system for sampling the metal ions in the corrosive gas according to claim 1, further comprising a weight detection device, wherein the weight detection device is configured to support the sampling bottle, and the weight detection device is configured for detecting a weight change value of the sampling bottle.

5. The system for sampling the metal ions in the corrosive gas according to claim 1, wherein materials for the sampling bottle and the injection pipeline both are perfluoroalkoxy.

6. A sampling method using the system for sampling the metal ions in the corrosive gas according to claim 1, comprising the following steps:
A1: closing the discharge valve, the injection valve, and the purge valve and opening the vacuum power valve, the first vacuuming valve, the second vacuuming valve, and the first valve to make a gas source enter the vacuum power pipeline and the gas inlet port of the vacuum generator through the gas source inlet and then flow out through the gas outlet port of the vacuum generator, such that the negative pressure port of the vacuum generator generates a negative pressure to vacuum the second vacuum pipeline, the third vacuum pipeline, the first sampling pipeline, the purge gas pipeline, and the sampling bottle;
A2: closing the vacuum power valve, the first vacuuming valve, and the second vacuuming valve and opening the discharge valve and the purge valve, such that a replacement gas source enters the purge gas pipeline through the gas source inlet, flows into the first sampling pipeline and the sampling bottle, and then flows out through the second sampling pipeline;
A3: alternately conducting the step A1 and the step A2 multiple times with the step A1 as a last step, and closing the vacuum power valve, the first vacuuming valve, and the second vacuuming valve;
A4: closing the discharge valve and the first valve and opening the injection valve to make a low-pressure liquefied gas to be sampled introduced into the sampling bottle, and collecting the low-pressure liquefied gas to be sampled by the sampling bottle quantitatively, wherein a lower end of the first sampling pipeline is located under a liquid level of a sampled low-pressure liquefied gas, and a lower end of the second sampling pipeline is located above the liquid level of the sampled low-pressure liquefied gas; and
A5: closing the injection valve and opening the purge valve, the first valve, and the discharge valve to make a purge gas source enter the purge gas pipeline through the gas source inlet and then flow into the first sampling pipeline and the sampling bottle, wherein the purge gas is introduced at a flow rate of 100 mL/min to 200 mL/min to slowly vaporize a liquefied corrosive gas in the sampled low-pressure liquefied gas and purge a vaporized corrosive gas out of the sampling bottle through the second sampling pipeline, such that the metal ions remain in the sampling bottle.

7. The sampling method according to claim 6, wherein the purge gas pipeline is provided with a first shunt and a second shunt, and the first shunt and the second shunt are arranged in parallel; the first shunt is provided with a third valve and a fourth valve, and the first shunt is provided with a first mass flow rate controller; the first mass flow rate controller is arranged between the third valve and the fourth valve;
the second shunt is provided with a second mass flow rate controller, and the second shunt is provided with a fifth valve and a sixth valve; the second mass flow rate controller is arranged between the fifth valve and the sixth valve; and a junction of the second vacuum pipeline and the purge gas pipeline is located between the purge valve and the first shunt as well as the second shunt;
in the step A1, while the vacuum power valve, the first vacuuming valve, the second vacuuming valve, and the first valve are opened, the third valve and the fourth valve are opened and/or the fifth valve and the sixth valve are opened to vacuum the first shunt and/or the second shunt; and
in the step A5, while the purge valve, the first valve, and the discharge valve are opened, the third valve and the fourth valve are opened and/or the fifth valve and the sixth valve are opened, and the first mass flow rate controller and/or the second mass flow rate controller control(s) the flow rate of the purge gas.

8. A sampling method using the system for sampling the metal ions in the corrosive gas according to claim 1, comprising the following steps:
B1: adding an absorption solution configured for dissolving the metal ions to the sampling bottle, wherein a lower end of the first sampling pipeline is located under a liquid level of the absorption solution, and a lower end of the second sampling pipeline is located above the liquid level of the absorbing solution; and
B2: closing the first valve and opening the discharge valve and the injection valve, such that a high-pressure liquefied gas to be sampled is introduced into the sampling bottle to enter the absorption solution, metal ions in a sampled high-pressure liquefied gas are dissolved in the absorption solution, and a treated corrosive gas is discharged through the discharge valve.

* * * * *